US00PP30650P2

(12) United States Plant Patent
Hansen

(10) Patent No.: US PP30,650 P2
(45) Date of Patent: Jul. 2, 2019

(54) **X *MANGAVE* PLANT NAMED 'FALLING WATERS'**

(50) Latin Name: ***Manfreda* times *Agave*, known as X *Mangave***
Varietal Denomination: Falling Waters

(71) Applicant: Hans A. Hansen, Zeeland, MI (US)

(72) Inventor: Hans A. Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 15/932,741

(22) Filed: Apr. 18, 2018

(51) Int. Cl.
*A01H 5/12* (2018.01)
*A01H 6/12* (2018.01)

(52) U.S. Cl.
USPC ..... Plt./373

(58) Field of Classification Search
USPC ..... Plt./373
See application file for complete search history.

(56) References Cited

PUBLICATIONS

Walters Garden Summer 2017-Spring 2018 Catalog. https://www.provenwinners.com/sites/provenwinners.com/files/images/professional/catalogs/1-intro-pw_perennials_2018.pdf. 5 pages.*

* cited by examiner

*Primary Examiner* — Susan McCormick Ewoldt
*Assistant Examiner* — Karen M Redden

(57) ABSTRACT

A new and unique X *Mangave* plant named 'Falling Waters' characterized by a medium mound of broad, fleshy, longitudinally folded, medium green foliage that is cascading, and with faint spots that intensify from moderate yellow-green to mahogany-colored with greater ultraviolet light exposure. The new plant is suitable for the garden or as a potted plant in the garden or home.

1 Drawing Sheet

Botanical classification: hybrid; *Manfreda* times *Agave*, known as X *Mangave*.

Variety denomination: 'Falling Waters'.

BACKGROUND OF THE INVENTION

The present invention relates to the new and distinct X *Mangave* hybrid plant, X *Mangave* 'Falling Waters' hybridized by the inventor at a wholesale perennial nursery in Zeeland, Mich., USA as cross between a proprietary unnamed *Manfreda maculosa* (not patented) as the female or seed parent times an unnamed selection of *Agave ovatifolia* (not patented) as the male or pollen parent. The cross was performed on Jun. 4, 2012 and seeds were harvested and sown later in October of 2012. Through trials at the same nursery the plant was assigned the breeder code XMANG-12-52-08. The new plant has been successfully asexually propagated initially by sterile shoot-tip tissue culture at the same nursery in Zeeland, Mich. Both methods of asexual propagation systems have been found to produce stable and identical plants that maintain all the unique characteristics of the original plant.

No plants of X *Mangave* 'Falling Waters' have been sold, under this or any name, in this country or anywhere in the world, prior to the filing of this application, nor has any disclosure of the new plant been made prior to the filing of this application with the exception of that which was disclosed or sold within one year of the filing of this application, and was either derived directly or indirectly from the inventor.

BRIEF SUMMARY OF THE INVENTION

X *Mangave* 'Falling Waters' differs from its parents as well as all other *Manfreda, Agave* and X *Mangave* known to the applicant. The female parent has foliage that is narrower and more linear, thinner in cross section, has smaller marginal teeth, leaves are more succulent, with more significant mahogany spotting and less arching. The male parent has foliage that is more ovate and compact, flatter, with larger marginal teeth, more fibrous, and no mahogany spotting. The nearest comparison plant is X *Mangave* 'Whale Tale' U.S. Plant patent application Ser. No. 15/932,526. 'Whale Tale' has more and larger greyed-purple spotting, more glaucous foliage, the marginal teeth are not as pronounced, and the foliage is more outright and less arching. Other similar cultivars include: 'Catch a Wave' U.S. Plant Pat. No. 29,723 and 'Silver Fox' U.S. Plant Pat. No. 29,642. 'Catch a Wave' has more sinuate, less arching foliage that is more heavily spotted. 'Silver Fox' has more pruinose foliage that is less arching and the habit is smaller.

The new plant, 'Falling Waters', is unique from all of the above cultivars and all *Agave*, X *Mangave* and *Manfreda* know to the inventor by the following combined traits:

1. Medium mound of medium green lanceolate, broad, fleshy, longitudinally folded foliage;
2. Foliage has faint spots that become more pronounced mahogany-colored in strong ultraviolet light;
3. Leaf margins deeply scalloped with small teeth;
4. Moderate growth rate.
5. Foliage cascades or arches with age.

BRIEF DESCRIPTION OF THE DRAWING

The photograph of x *Mangave* 'Falling Waters' demonstrates the overall appearance of the new plant including the unique traits as a three-year-old plant grown in a container in a greenhouse with supplemental water and fertilizer as needed. The colors are as accurate as reasonably possible with color reproductions. Ambient light spectrum, temperature, source and direction may cause the appearance of minor variation in color.

The illustration shows the new plant with conduplicate foliage, teeth and apical spines.

DETAILED BOTANICAL DESCRIPTION

The following descriptions and color references are based on the 2015 edition of The Royal Horticultural Society Colour Chart except where common dictionary terms are used. The new plant, X *Mangave* 'Falling Waters', has been observed under all possible environments. The phenotype may vary slightly with different environmental conditions, such as temperature, light, fertility, moisture and maturity levels, but without any change in the genotype. The following observations and size descriptions are of a three-year old plant in a commercial wholesale greenhouse in Zeeland, Mich. with supplemental water and fertilizer as needed.

Parentage: An unnamed select form of *Manfreda maculosa* as female or seed patent and an unnamed select form of *Agave ovatifolia* as male or pollen parent;

Propagation: By sterile shoot-tip tissue culture;

Time to initiate roots from tissue culture: About 21 days;

Growth rate: Moderate;

Crop time: About 12 to 16 weeks to finish in a 3.8 liter container from a 35 mm tissue culture growing at about 21° C.;

Rooting habit: Fleshy, lightly branching, with roots up to 20 cm long;

Root color: Nearest RHS 158C;

Plant shape and habit: Succulent herbaceous perennial with basal rosettes of about 48 leaves radially emerging outwardly from central stem, producing a radially-symmetrical, rounded mound;

Plant size: Foliage height about 38.0 cm tall from soil line to the top of the leaves and about 76.0 cm wide at the widest point slightly below soil line in container;

Foliage description: Lanceolate; simple; sessile; bi-laterally symmetrical; apex acute with terminal spine; terminal spine to about 12.0 mm long; base truncate; conduplicate, especially young leaves; margins coarsely irregularly dentate; glaucous waxy bloom abaxial and adaxial without trichomes; with abaxial and adaxial spots about 2.0 mm to 3.0 mm long and wide rarely touching or overlapping;

Teeth: Initially flexible, becoming hard and sharp with age; about 1.0 mm long and 1.0 mm long on end of protrusion about 4.0 mm long and about 3.5 mm wide at base; protrusions average about 9.0 mm apart on mature leaves;

Leaf size: To about 30.0 cm long, about 9.0 cm wide toward base; and about 5.0 mm thick at base; average about 28.0 cm long, 8.0 cm wide and 4.0 mm thick;

Foliage fragrance: None observed;

Leaf number: About 47 per plant;

Leaf blade color:

*Adaxial* (*young*).—Nearest RHS N138C with spots nearest RHS 137A in low ultraviolet light intensifying with high ultraviolet exposure to nearest RHS N187A.

*Abaxial* (*young*).—Nearest RHS N138C with spots nearest RHS 137A in low ultraviolet light intensifying with high ultraviolet exposure to nearest RHS N187A.

*Adaxial* (*mature*).—Between RHS 137D and RHS 138A with spots intensifying with ultraviolet light exposure nearest RHS N187A.

*Abaxial* (*mature*).—Between RHS 138B and RHS 137D.

*Teeth*.—Beginning nearest RHS 160D and maturing to nearest RHS 166A.

Petiole: Leaves sessile;

Veins: Parallel; not distinct abaxial or adaxial;

Flower description: Not yet observed to date;

Fruit and seed: Not observed to date;

Disease resistance: X *Mangave* 'Falling Waters' has not been observed to be resistant to diseases beyond that which is normal for X *Mangave, Agave* or *Manfreda*. The new plant is xeromorphic and survives well with minimal water once established. The new plant is estimated to be hardy at least from USDA zone 7b. Full extent of winter hardiness has not been tested.

It is claimed:

1. A new and distinct cultivar of ornamental X *Mangave* plant named 'Falling Waters' as herein described and illustrated.

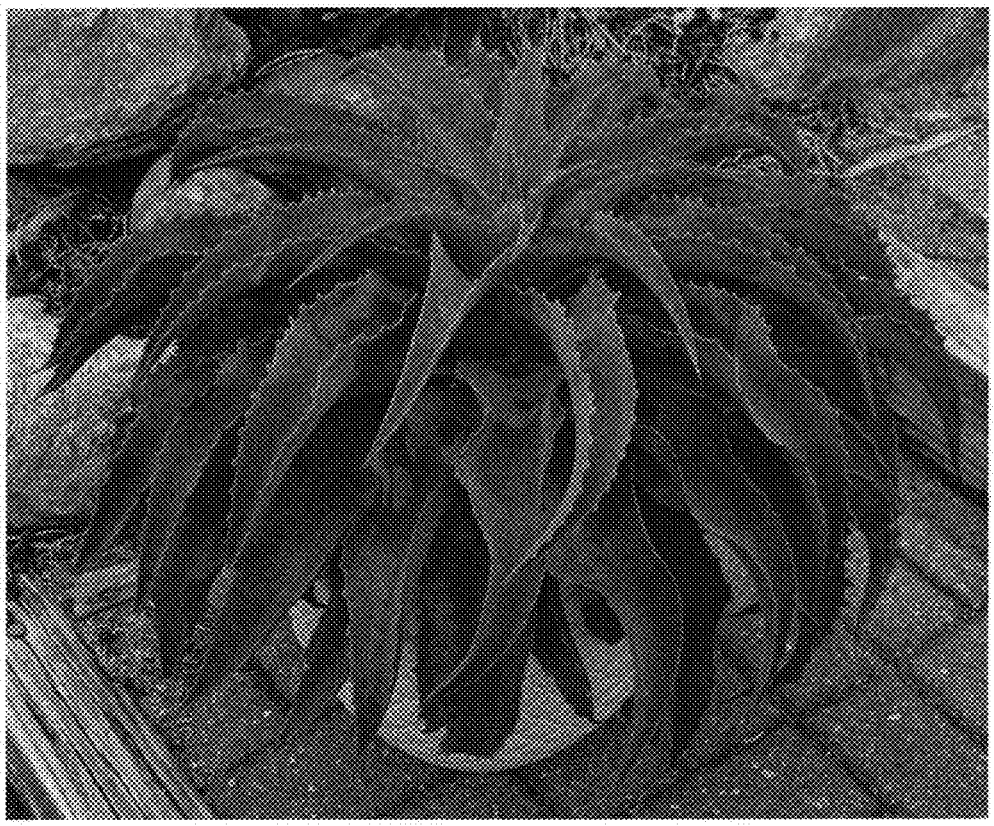

* * * * *